United States Patent [19]

Henry et al.

[11] Patent Number: 4,798,539

[45] Date of Patent: Jan. 17, 1989

[54] PRENATAL LEARNING DEVICE AND METHOD

[76] Inventors: Verlyn Henry; Danise Henry, both of 8130 Kendaville Rd., Lakeview, Mich. 48850

[21] Appl. No.: 30,344

[22] Filed: Mar. 26, 1987

[51] Int. Cl.⁴ .......................................... G09B 50/004
[52] U.S. Cl. ...................................... 434/319; 224/224
[58] Field of Search ............... 434/319; 224/224–230, 224/236, 242, 251; 455/100, 89; 128/660, 24 A, 24.1, 24.2, 24.5, 384, 802, 1 R

[56] References Cited

U.S. PATENT DOCUMENTS

| | | | | |
|---|---|---|---|---|
| D. 278,761 | 5/1985 | Fuller | ................................ | 434/319 |
| 2,298,600 | 10/1942 | Stember | ............................. | 224/228 |
| 4,073,416 | 2/1978 | McComber | ......................... | 224/224 |
| 4,450,495 | 5/1984 | Naruki | .................................. | 455/89 |
| 4,569,465 | 2/1986 | O'Farrell | ............................ | 434/319 |
| 4,620,653 | 11/1986 | Farrell | ................................. | 224/242 |

*Primary Examiner*—Richard J. Apley
*Assistant Examiner*—J. Welsh
*Attorney, Agent, or Firm*—Price, Heneveld, Cooper, DeWitt & Litton

[57] ABSTRACT

A method and device for transmitting sonic vibrations, such as music, to a fetus includes an abdominal belt to be worn by the mother. The belt is equipped with either a compact cordless cassette player or a radio receiver or simply a speaker or speakers powered from a remote player and power pack. The belt is provided with pockets for detachably receiving the equipment so that it can be removed for laundry or dry cleaning of the belt.

25 Claims, 2 Drawing Sheets

PRENATAL LEARNING DEVICE AND METHOD

FIELD OF THE INVENTION

The invention relates to a method for prenatal education and communication including the use of devices for transmitting sonic vibrations to a fetus while in the womb. The device permits the parent to determine what, when and how much is transmitted.

BACKGROUND OF THE INVENTION

It has long been recognized that the human fetus, after a certain point in its development, will respond to external stimuli such as tapping on the mother's abdomen. It is further known that, as the fetus nears full development, the fetus will imitate patterns of vibration which are transmitted to it. However, no one has heretofore conceived for systematically communicating with and educating a baby in its mother's womb, especially in the manner encompassed by the present invention.

SUMMARY OF THE INVENTION

The present invention comprises a method and device for systematically educating and communicating with a baby in its mother's womb. Means for broadcasting a message, music or other desired sounds to the baby are located within means for positioning the broadcast means adjacent the mother's womb.

Preferably, the positioning means includes sound insulation means for minimizing the transmission of sound anyplace but to the womb. Also preferably, educational or like messages are prerecorded for broadcast to the baby, whereby the mother can be occupied in other pursuits while the message is being broadcast to the baby.

These and other objects, advantages and features of the invention will be more fully understood and appreciated by reference to the written specification and appended drawings.

DESCRIPTION OF THE PREFERRED EMBODIMENT

Figure 1:
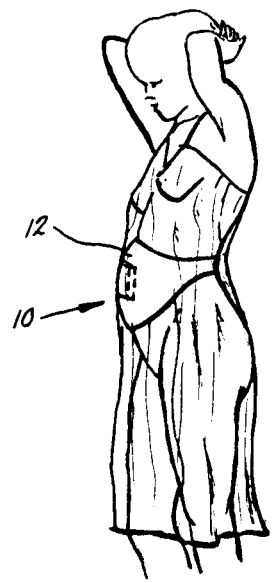
FIG. 1 illustrates the intended use and location of the invention by the mother.
Figure 3:
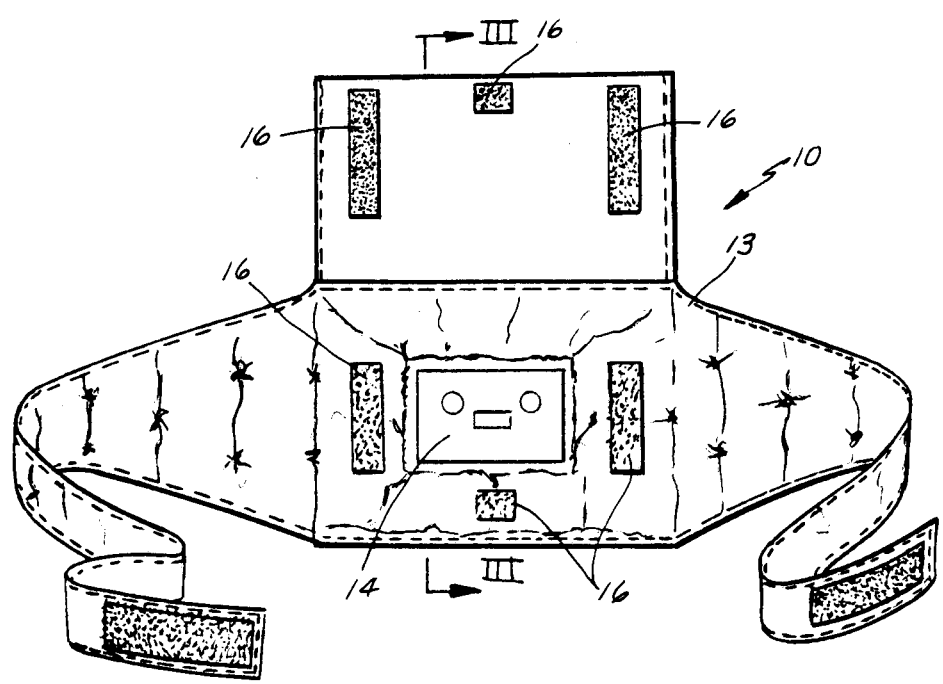
FIG. 3 is a sectional view taken along the plane III—III of FIG. 2.

In the preferred embodiment, the device of the present invention includes a belt 10 to be worn around the abdomen of the mother (FIG. 1). Belt 10 has a pocket 13 in which a broadcasting device is placed (FIG. 3). The broadcasting device could be any of a number of different types, such as a miniature tape player, a compact radio receiver or simply a compact speaker wired to a remote signal source. Between this unit and the mother's body a layer 15 of suitable material, such as by an envelop-like flap so lined, is provided so that the unit will not create a hard, concentrated source of pressure against the mother's abdomen. However, the material of this layer has to be selected from materials which will not absorb and thereby not transmit the sonic vibrations, especially the soft, less penetrating sounds that are associated with soothing melodies such as lullabies.

Figure 2:
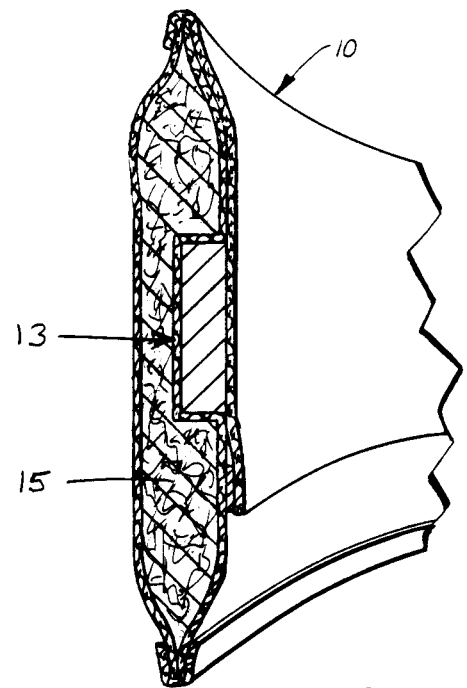
FIG. 2 is an elevation view of the inside surface of the belt for supporting the unit.

The length of belt 10 is such that it can be wrapped about the user's abdomen and secured by suitable means such as strips 11 of fastener material such as Velcro, a trademark of Velcro USA Inc., Manchester, New Hampshire. Snap fasteners, buttons or the like could be substituted for Velcro. The ends of the belt on which the fastener strips are mounted are narrowed to form straps to facilitate use and reduce bulk. The central section 12 of the belt, that being the portion which will overlie the abdomen when in use, is thicker and wider than the rest of the belt. Substantially centered in this section is a recessed pocket 13. The pocket is provided to support the source of the sonic vibrations which are the object of this invention. The size and shape of the pocket may vary, depending upon the equipment which will be mounted in the pocket. The particular equipment, illustrated in FIGS. 2 and 3, is a compact, cordless cassette player 14. Preferably, it is so constructed that its vibration source or transducer faces the inside surface of the belt. The walls of the pocket hold the player in place. The pocket is closed by a fabric cover or flap 15 hinged at the top and secured in closed position by suitably positioned strips 16 of material such as Velcro.

The belt must be of soft material and capable of readily flexing and of being easily shaped to conform to the user's body. Further, at least that portion of it which forms the flap 15 must be capable of transmitting sound waves rather than absorbing them. An example of a construction which has been found satisfactory is an outer envelop of a fine, closely woven fabric consisting of a mixture of about 65% polyester and 35% cotton similar to a percale. The envelope has a filling or polyester fibers, such as those used as the filler in pillows. After the filling has been placed in the envelop, the belt is tufted or quilted to stabilize the position of the filling. It has been found that a thin layer of the polyester fibers in the flap does not interfere with the transmission of the sonic vibrations through the flap.

Figure 4:
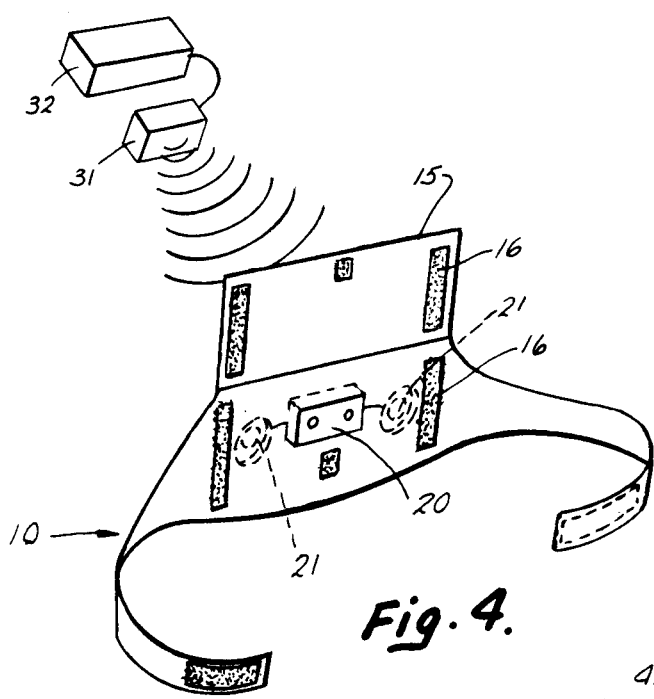
FIG. 4 is a somewhat schematic view of a modified arrangement incorporating this invention.
Figure 6:
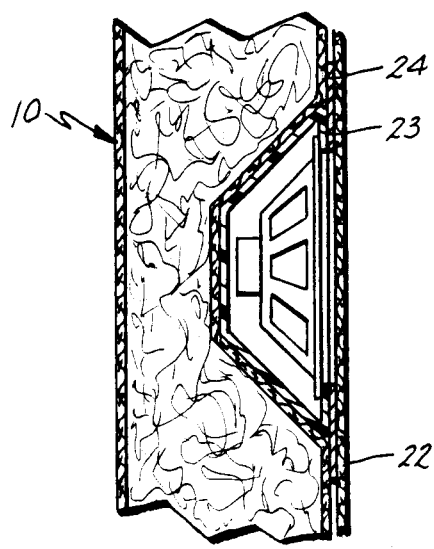
FIG. 6 is a fragmentary, enlarged, partially sectional view of the mounting of a typical speaker.

FIG. 4 illustrates a modification of the invention in which a small radio receiver 20 is substituted for the cassette player 14. The receiver 20 is powered by batteries which may be stored in the player or in a separate pouch the mother may wear elsewhere. The receiver 20 may have its own built-in speaker or, as illustrated, the speaker may be a separate unit and may even consist of a pair of speakers 21 to provide a stereophonic effect. When the speakers are separate units, they are mounted inside a protective shell 22 which has flanges 23 secured to the inside face of the inner layer of fabric forming the belt's envelop by Velcro 24 (FIG. 6). Other detachable means of securing the shell include snap fasteners or buttons. Whatever attachment means is used, it should permit the speaker and its protective shell to be removed so the belt can be laundered or dry cleaned. The protective shell is preferably a molded plastic component molded from a suitable material such as polypropylene or styrene. The wires connected to the speaker should lay on the surface of the pocket under the flap so that they also are removable with the speaker. The mounting of the speaker within the shell would be such as not to adversely affect the speaker's ability to produce the desired sound. Accomplishing this is conventional practice in the art of audio reproduction.

When a radio receiver is used as indicated in FIG. 4, the receiver 20 is preferably low powered to avoid reception of extraneous and unwanted signals. The source of the radio signals can be a very low powered transmitter 31 located in the same room or living quarters. The transmitter 31 may obtain its program from a tape deck or the like 32. The system illustrated in FIG. 4 has the advantage of keeping to a minimum the bulk and weight of the belt and its related equipment which the mother must carry. At the same time, the mother is free to move about and do whatever she wants or needs to do without interfering with the actual function of the equipment in delivering sound vibrations to the fetus.

Figure 5:
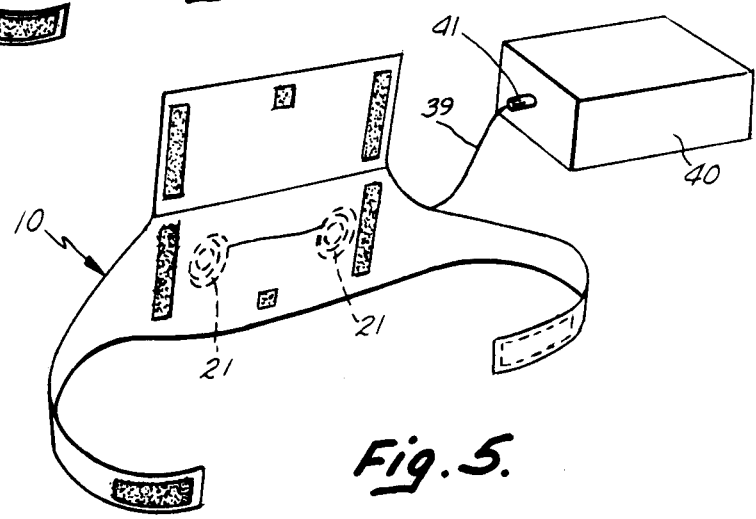
FIG. 5 is a somewhat schematic view of a further modified arrangement incorporating this invention.

FIG. 5 illustrates another modification in which the belt only mounts one or a pair of speakers. These speakers are connected by cable 39 to a signal source, such as a cassette player 40. The player can be carried by the mother or it can be worn by the mother as a separate pack. The signal source is made disconnectable by a cable plug 41. Once again, the speaker should be removably mounted to the belt and the cable to the signal source should be on the surface behind the flap covering the pocket and should emerge from behind the flap at a suitable point for connection to the signal source.

In the case of each of the equipment arrangements which have been described, the mother has full control of the timing and length of the sound program transmitted. The mother also has control of the content and, in some cases, may be able to make some assessment as to the effect of the transmissions on the fetus. The audio level is very low. Thus, in many cases, the mother can be using this invention without people around her being aware of that fact, particularly if the filler in the belt behind the speaker is of a sound absorbing material. The invention can be practiced using simple, compact and relatively inexpensive equipment and can be used repeatedly.

The belt could be so made that it will accommodate any of the equipment combinations which have been described. Thus, it could have a central pocket for either the cassette player or the radio receiver and a pair of spaced pockets for the separate speakers. Only those pockets would be used at any one time which are required by the equipment then in use. All of the equipment could be located in a single pocket or various items of the equipment could be located in separate pockets.

In use, educational messages or soothing messages are communicated to the baby by means of the broadcast device. Prerecorded educational tapes can be employed in the broadcast device. Professional taped educational messages could be used. Alternatively, the mother and father themselves could tape educational messages with their own voices. Such messages could comprise the A, B, C's, the presentation of simple words, the presentation of numbers, and etc. Nursery rhymes could be broadcast. Soothing music can be played. Soothing messages by the mother and father can be prerecorded and communicated to the baby.

By using prerecorded messages, the mother is free to go about her day's work while the baby is being educated or lulled to sleep in its mother's womb. By providing adequate sound insulation, the sound of the broadcast device is directed only towards the baby in the womb and is not heard by the mother or others around her.

Having described a preferred embodiment of my invention and several modifications of it, it will be understood that other modifications can be made without departing form the principles of the invention. Such modifications are to be considered as included in the hereinafter appended claims unless the claims, by their language, expressly state otherwise.

The embodiments of the invention in which an exclusive property or privilege is claimed are defined as follows:

1. A method for educating and communicating with a fetus in its mother's womb comprising:
   mounting a sonic source means for transmitting a communication to a fetus in its mother's womb in a support and positioning means, and securing said support and positioning means to a mother with said sonic source means located adjacent to and in sonic vibration transmitting relation to the mother's womb; and
   transmitting a desired communication in sonic wave form into the womb from said sonic source means.

2. The method of claim 1 which includes prerecording desired communications and providing means for generating said prerecorded communications in sonic form through said sonic source means.

3. The method of claim 2 which comprises prerecording educational messages.

4. The method of claim 2 which comprises prerecording nursery rhymes for transmission through said sonic source means.

5. The method of claim 2 which comprises prerecording soothing communications and transmitting them through said sonic source means.

6. The method of claim 2 in which said communications are prerecorded by a parent of the fetus.

7. The method of claim 1 which includes providing sound insulation means on all sides of said sonic source means except the side oriented towards the mother's womb whereby the transmission of sound other than in the direction of the mother's womb is minimized.

8. A device for communicating with a unborn fetus comprising:
   a sonic source means for generating in sonic form a communication to a fetus in its mother's womb;
   said sonic source means being mounted on positioning means;
   said positioning means including support means for securing said positioning means on a mother's body with said sonic source means adjacent her womb;
   said sonic source means being oriented on said positioning means to face and transmit sonic vibrations to the mother's womb when said positioning means is secured to the mother;
   sound insulation means located in said positioning means around said sonic source means on all sides except that oriented towards the mother's womb whereby sound from said sonic source means is not substantially transmitted in any direction except towards the mother's womb.

9. The device of claim 8 in which said broadcast means comprises a portable source of audible sound removably secured to said positioning means.

10. The device of claim 8 in which said sonic source means comprises a portable tape player and recorder removably secured to said positioning means.

11. The device of claim 10 in which said positioning means comprises a belt including means for releasably securing said belt around a mother's abdomen.

12. The device of claim 8 in which said broadcast means comprises a portable tape player and recorder removably secured to said positioning means.

13. The device of claim 8 in which said positioning means comprises a belt including means for releasably securing said belt around a mother's abdomen.

14. Means transmitting sonic vibrations to a fetus, said means comprising a generator of sonic vibrations, a support belt for said generator of a length to be worn by the mother while wrapped around the abdomen with said generator being positioned in front of the mother, said belt having a pocket for receiving the generator and flap means on the inside of the belt for covering said pocket to retain said generator, said flap being constructed of materials which d ont interfere with the transmission of the generator created vibrations, the walls of said pocket except said flap, being lined with soft sound absorbing padding to reduce the transmission of sonic vibrations in any direction other than through said flap, said generator being an electrical transducer and a signal source for actuating said transducer.

15. The means described in claim 14 wherein said signal source is remote from said transducer and connected thereto by a signal transmitting means.

16. The means described in claim 15 wherein said signal source is connected to said transducer by an electrical conductor.

17. The means described in claim 15 wherein said signal source is a source of radio waves remote from said transducer and a radio wave receiving means operatively connected to said transducer.

18. The means described in claim 15 wherein said signal source is a cassette player for a recording.

19. The means described in claim 14 wherein a pair of said sonic vibration generators are mounted on said belt in spaced apart relationship.

20. Means for transmitting sonic vibrations to a fetus, said means comprising: a generator of sonic vibrations, a support belt for said generator of a length to be worn by the mother while wrapped around the abdomen, said belt having a recessed pocket for receiving and supporting said generator immediately contiguous to the mother's abdomens, a flap for enclosing said pocket; means securing said flap to said belt along one of its edges and detachable means securing said flap in pocket closing position, said belt having a washable fabric envelop enclosing an inner layer of synthetic fibers forming a soft compressible mass capable of being laundered, said envelop being tufted to retain said fibers in position; said flap being lined with fibrous material which does not interfere with the transmission of sonic vibrations therethrough.

21. The means described in claim 20 wherein said belt has a plurality of pockets for receiving various types of equipment, all of said pockets being covered by flap means when the flap means is closed.

22. The method of transmitting information to an unborn fetus, providing the mother with a sonic vibration generating source; attaching the generating source to the mother's abdomen and providing means for activating the generating source, controlling the generating source to produce sonic vibrations in a selected pattern for producing a desired response on the part of the fetus.

23. The method recited in claim 22 including the additional step of limiting the sonic vibrations to those produced by musical instruments arranged in a predetermined sequence.

24. Means for transmitting sonic vibrations to a fetus, said means comprising: a transducer for creating sonic vibrations; a support belt for said transducer of a length to be worn by the mother while wrapped around the abdomen, said belt having a recessed pocket for receiving and supporting said transducer immediately contiguous to the mother's abdomen, a flat for enclosing said pocket; means securing said flap to said belt along one of its edges and detachable means securing said flat in pocket closing position, said belt having a washable fabric envelop enclosing an inner layer of sound absorbing synthetic fibers forming a soft compressible mass encasing all of the transducer except that part of the transducer facing said flap, said envelop and synthetic fibers being capable of being laundered, detachable means for securing said transducer to said belt.

25. Means for transmitting sonic vibrations to a fetus as described in claim 24 wherein said flap is an envelope lined with a moisture nonabsorbant, fibrous material which does not interfere with the transmission of sonic vibrations therethrough.

* * * * *

UNITED STATES PATENT AND TRADEMARK OFFICE
CERTIFICATE OF CORRECTION

PATENT NO. : 4,798,539

DATED : January 17, 1989

INVENTOR(S) : Verlyn and Danise Henry

It is certified that error appears in the above-identified patent and that said Letters Patent is hereby corrected as shown below:

Column 4, Line 4:

"form" should be --from--.

Column 4, Claim 8, Line 41:

"a" should be --an--.

Column 5, Claim 14, Line 15:

"d ont" should be --do not--.

Column 5, Claim 20, Line 43:

"abdomens" should be --abdomen--.

Column 6, Claim 24, Line 30:

"flat" should be --flap--.

UNITED STATES PATENT AND TRADEMARK OFFICE
CERTIFICATE OF CORRECTION

PATENT NO. : 4,798,539

DATED : January 17, 1989

INVENTOR(S) : Verlyn and Danise Henry

It is certified that error appears in the above-identified patent and that said Letters Patent is hereby corrected as shown below:

Column 6, Claim 24, Line 32:

"flat" should be --flap--.

Signed and Sealed this

Ninth Day of January, 1990

*Attest:*

JEFFREY M. SAMUELS

*Attesting Officer*     *Acting Commissioner of Patents and Trademarks*